United States Patent [19]
Cullinan et al.

[11] Patent Number: 5,929,092
[45] Date of Patent: Jul. 27, 1999

[54] LIPOPHILIC BENZOTHIOPHENES FOR TREATING ESTROGEN DEFICIENCY

[75] Inventors: George Joseph Cullinan, Trafalgar; Raymond Francis Kauffman, Carmel, both of Ind.

[73] Assignee: Eli Lilly and Company, Indianapolis, Ind.

[21] Appl. No.: 08/943,749

[22] Filed: Oct. 3, 1997

Related U.S. Application Data

[62] Division of application No. 08/707,680, Sep. 4, 1996, Pat. No. 5,726,168.
[60] Provisional application No. 60/005,140, Oct. 12, 1995.
[51] Int. Cl.$^6$ ........................ A61K 31/445; C07D 333/52
[52] U.S. Cl. ........................ 514/324; 514/176; 514/422; 546/202; 548/525
[58] Field of Search ........................ 546/202; 548/525; 514/176, 324, 422

[56] References Cited

U.S. PATENT DOCUMENTS

| | | | |
|---|---|---|---|
| 4,133,814 | 1/1979 | Jones et al. | 546/202 |
| 4,418,068 | 11/1983 | Jones | 546/202 |
| 5,726,168 | 3/1998 | Cullinan | 514/176 |

FOREIGN PATENT DOCUMENTS

| | | |
|---|---|---|
| 0641791 A1 | 5/1993 | European Pat. Off. |
| 617030 A1 | 3/1994 | European Pat. Off. |
| 0605193 A1 | 7/1994 | European Pat. Off. |
| 652003 A1 | 10/1994 | European Pat. Off. |
| 0674903 A1 | 10/1995 | European Pat. Off. |

OTHER PUBLICATIONS

Wyngaarden et al. "Cecil textbook of medicine" Sauders Co. pp. 1272, 1332, 1983.
Oparil "Hypertension in postmenopausal women:pathophysiology and management" EMBASE:95283951, 1995.
Insua et al. "Postmenopause, plasma lipoproteins and hormone replacement therapy" Indexmedicus 94:260928, 1994.
Ebeling et al. "Bone turnover markers and bone density across the menopausal transition" indexmedicus 96:378535, 1996.
Haudenschild, Christian C., "Pathobiology of Restenosis After Angioplasty", *American Journal of Medicine*, 94, 40–44 (1993).
Wilensky, Robert L. et al., "Methods and Devices for Local Drug Delivery in Coronary and Peripheral Arteries", *Trends Cardiovasc Med*, 3, 163–170 (1993).
Waller, Bruce F. et al., "Morphologic Observations Late After Coronary Balloon Angioplasty: Mechanisms of Acute Injury and Relationship to Restenosis[1]", *Radiology*, 174, 961–967 (1990).

*Primary Examiner*—Ceila Chang
*Attorney, Agent, or Firm*—Gilbert T. Voy; James J. Sales

[57] ABSTRACT

The invention provides novel benzothiophenes of the formula (I):

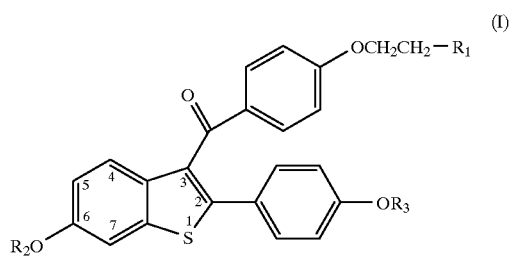

wherein $R_1$ is N-pyrrolidinyl or N-piperidinyl;

$R_2$ and $R_3$ are independently hydrogen, —CO—($C_{10}$–$C_{22}$ alkyl), —CO—($C_{10}$–$C_{22}$ branched alkyl), —CO—($C_{10}$–$C_{22}$ alkenyl), —CO—($C_{10}$–$C_{22}$ polyalkenyl), —CO—($C_{10}$–$C_{22}$ alkynyl), or —CO—$(CH_2)_n COR_4$; provided $R_2$ and $R_3$ are not both dodecanoyl, and one of $R_2$ or $R_3$ is not hydrogen $R_4$ is -3-cholesteryl or —O$(CH_2)_2(OR_5)CH_2OR_6$;

$R_5$ and $R_6$ are independently hydrogen, —CO—($C_{10}$–$C_{22}$ alkyl), —CO—($C_{10}$–$C_{22}$ branched alkyl), —CO—($C_{10}$–$C_{22}$ alkenyl), —CO—($C_{10}$–$C_{22}$ polyalkenyl), or —CO—($C_{10}$–$C_{22}$ alkynyl); provided one of $R_5$ or $R_6$ is not hydrogen;

n is 0–4; and pharmaceutically acceptable salts and solvates thereof, and further provides pharmaceutical compositions containing compounds of formula I, and the use of such compounds.

8 Claims, No Drawings

LIPOPHILIC BENZOTHIOPHENES FOR TREATING ESTROGEN DEFICIENCY

This application is a division of application Ser. No. 08/707,680 filed Sep. 4, 1996, now U.S. Pat. No. 5,726,168, which was based on U.S. Provisional Application 60-005,140 filed on Oct. 12, 1995.

BACKGROUND OF THE INVENTION

There are three types of lesions found in the arteries which are associated with atherosclerosis: fatty streaks, fibrous plaques, and complicated plaques. Fatty streaks occur early in life and consist of an accumulation of lipid-filled macrophages and smooth muscle cells (foam cells) and accumulated fibrous tissue on the intima. In general, these fatty streaks appear not to be particularly dangerous in themselves; however, they may be contributory to the formation of fibrous plaques. Fibrous plaques are raised lesions on the intima. These plaques consist of a central core of extracellular lipid and necrotic cell debris and are covered with an overlayment of smooth muscle cells and collagen matrix. This makes the fibrous plaque foci, a place of constricted blood flow in the artery. The fibrous plaque is characteristic of advancing atherosclerotic disease. The complicated plaque is a calcified fibrous plaque and is an area of thrombosis, necrosis, and ulceration. This plaque constricts the blood flow and causes stenosis that can lead to organ insufficiency. The site of a complicated plaque is, also, an area of weakened arterial wall which may fail, causing aneurysm formation and hemorrhaging.

One theory of atherogensis is the reaction-to-injury hypothesis. According to this hypothesis, the lining endothelial cells of the artery are exposed to acute, repeated acute, or chronic injury, which causes the cells to detach from one another, thus exposing the underlying connective tissue bed. This break in the continuous system of endothelium elicits platelet adhesion, aggregation, and the formation of microthrombi. This platelet interaction causes the release of mitogenic factors leading to the proliferation of smooth muscle cells, the production of matrix, and the trapping of lipids from the serum. Although this repairs the immediate break in the system, the disturbance in the blood around the lesion often causes further damage to endothelium in adjacent areas, especially down stream from the initial insult, thus increasing the plaque size. This process continues to build the lesion and leads to constriction of the blood flow and eventual occlusion or failure of the arterial wall.

Today, balloon angioplasty is one of the most common procedures used in treating atherosclerotic plaques, especially for relatively small plaques. It is often preferred over by-pass surgery, in that it is less expensive and is a great deal less traumatic to the patient.

Although angioplasty is very effective at initially opening the occluded artery, this artery often fails to remain open for an extended period of time. Within one year, 30–50% of the arteries opened by angioplastic surgery are occluded in the same or adjacent location as the initial blockage. The process by which this re-occlusion occurs is called restenosis. For reviews covering the morphologic changes and biopathology of restenosis following angioplasty see: Haudenschild, C. C., Am. J. of Med., 94, (Suppl 4A), p. 4A-40S–4A44S (1993) and Waller, B. F., et al. Radiology, 174,(3), p.961–967 (1990).

Currently, there is no treatment for the restenosis of an artery, other than repeating the angioplasty, which may exacerbate the problem, or performing a more extensive procedure such as by-pass surgery.

It has been shown that another benzothiophene, raloxifene (formula I, $R_1$ is n-piperidenyl, and $R_2$ and $R_3$ are hydrogen) is active in experimental models in inhibiting restenosis (see: EP652,003, published May 10, 1995). In experimental models conducted in vivo, raloxifene was administered via a systemic route (oral) demonstrating its beneficial effect at inhibiting restenosis. Additionally, it has now been shown that raloxifene is capable of inhibiting intimal thickening at a local site of angioplasty insult. This result is of great significance in that raloxifene is of a chemical class of compounds known as mixed estrogen agonist/antagonists, or SERMs, selective estrogen receptor modulators. Administration of a compound having a similar profile as that of raloxifene, but at the local site, would be an advantage for the treatment of restenosis induced by angioplastic intervention.

Ideally, it would be desirable to administer such an agent directly into the plaque at the time of angioplasty. This is problematic in that raloxifene is not very soluble in the highly lipophilic matrix found in the atherosclerotic plaque. Additionally, large volumes of solvent would be necessary to dissolve an effective amount of raloxifene which would then have to be delivered via the angioplasty catheter into the atherosclerotic plaque. Both of these raise practical concerns over the use of either raloxifene or its known derivatives from use as locally active agents for preventing restenosis via an angioplasty catheter.

It would be of great benefit if there were an efficient non-surgical treatment for restenosis. It would be of particular benefit if such a treatment could be confined to the immediate locality of the occluding plaque, since this would limit any potential side-effects of the treatment. A treatment such as a drug which could be delivered locally to the plaque site at the time of angioplasty and prevent restenosis at that site would be ideal.

"Post-menopausal syndrome" is a term used to describe various pathological conditions which frequently affect women who have entered into or completed the physiological metamorphosis known as menopause. Although numerous pathologies are contemplated by the use of this term, three major effects of post-menopausal syndrome are the source of the greatest long-term medical concern: osteoporosis, cardiovascular effects such as hyperlipidemia, and estrogen-dependent cancer, particularly breast and uterine cancer.

Osteoporosis describes a group of diseases which arise from diverse etiologies, but which are characterized by the net loss of bone mass per unit volume. The consequence of this loss of bone mass and resulting bone fracture is the failure of the skeleton to provide adequate structural support for the body. One of the most common types of osteoporosis is that associated with menopause. Most women lose from about 20% to about 60% of the bone mass in the trabecular compartment of the bone within 3 to 6 years after the cessation of mensus. This rapid loss is generally associated with an increase of bone resorption and formation. However, the resorptive cycle is more dominant and the result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is related with hip fractures in elderly women. A large percentage of this mortality rate can be directly associated with post-menopausal osteoporosis.

The most vulnerable tissue in the bone to the effects of post-menopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the bio-mechanical strength of the overall structure. In post-menopausal osteoporosis, it is, primarily, the net resorption and loss of the trabeculae which leads to the failure and fracture of bone. In light of the loss of the trabeculae in post-menopausal women, it is not surprising that the most common fractures are those associated with bones which are highly dependent on trabecular support, e.g., the vertebrae, the neck of the weight bearing bones such as the femur and the fore-arm. Indeed, hip fracture, collies fractures, and vertebral crush fractures are hallmarks of post-menopausal osteoporosis.

At this time, the only generally accepted method for treatment of post-menopausal osteoporosis is estrogen replacement therapy. Although therapy is generally successful, patient compliance with the therapy is low primarily because estrogen treatment frequently produces undesirable side effects.

Throughout premenopausal time, most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that post-menopausal women having estrogen replacement therapy have a return of serum lipid levels to concentrations to those of the pre-menopausal state. Thus, estrogen would appear to be a reasonable treatment for this condition. However, the side-effects of estrogen replacement therapy are not acceptable to many women, thus limiting the use of this therapy. An ideal therapy for this condition would be an agent which would regulate the serum lipid level as does estrogen, but would be devoid of the side-effects and risks associated with estrogen therapy.

The third major pathology associated with post-menopausal syndrome is estrogen-dependent breast cancer and, to a lesser extent, estrogen-dependent cancers of other organs, particularly the uterus. Although such neoplasms are not solely limited to a post-menopausal women, they are more prevalent in the older, post-menopausal population. Current chemotherapy of these cancers has relied heavily on the use of anti-estrogen compounds such as, for example, tamoxifen. Although such mixed agonist-antagonists have beneficial effects in the treatment of these cancers, and the estrogenic side-effects are tolerable in acute life-threatening situations, they are not ideal. For example, these agents may have stimulatory effects on certain cancer cell populations in the uterus due to their estrogenic (agonist) properties and they may, therefore, be contraproductive in some cases. A better therapy for the treatment of these cancers would be an agent which is an anti-estrogen compound having negligible or no estrogen agonist properties on reproductive tissues.

In response to the clear need for new pharmaceutical agents which are capable of alleviating the symptoms of, inter alia, post-menopausal syndrome, the present invention provides new benzothiophene compounds, pharmaceutical compositions thereof, and methods of using such compounds for the treatment of post-menopausal syndrome and other estrogen-related pathological conditions such as those mentioned below.

Uterine fibrosis (uterine fibroid disease) is an old and ever present clinical problem which goes under a variety of names, including uterine fibroid disease, uterine hypertrophy, uterine lieomyomata, myometrial hypertrophy, fibrosis uteri, and fibrotic metritis. Essentially, uterine fibrosis is a condition where there is an inappropriate deposition of fibroid tissue on the wall of the uterus.

This condition is a cause of dysmenorrhea and infertility in women. The exact cause of this condition is poorly understood but evidence suggests that it is an inappropriate response of fibroid tissue to estrogen. Such a condition has been produced in rabbits by daily administrations of estrogen for 3 months. In guinea pigs, the condition has been produced by daily administration of estrogen for four months. Further, in rats, estrogen causes similar hypertrophy.

The most common treatment of uterine fibrosis involves surgical procedures both costly and sometimes a source of complications such as the formation of abdominal adhesions and infections. In some patients, initial surgery is only a temporary treatment and the fibroids regrow. In those cases a hysterectomy is performed which effectively ends the fibroids but also the reproductive life of the patient. Also, gonadotropin releasing hormone antagonists may be administered, yet their use is tempered by the fact they can lead to osteoporosis. Thus, there exists a need for new methods for treating uterine fibrosis, and the methods of the present invention satisfy that need.

Endometriosis is a condition of severe dysmenorrhea, which is accompanied by severe pain, bleeding into the endometrial masses or peritoneal cavity and often leads to infertility. The cause of the symptoms of this condition appear to be ectopic endometrial growths which respond inappropriately to normal hormonal control and are located in inappropriate tissues. Because of the inappropriate locations for endometrial growth, the tissue seems to initiate local inflammatory-like responses causing macrophage infiltration and a cascade of events leading to initiation of the painful response. The exact etiology of this disease is not well understood and its treatment by hormonal therapy is diverse, poorly defined, and marked by numerous unwanted and perhaps dangerous side effects.

One of the treatments for this disease is the use of low dose estrogen to suppress endometrial growth through a negative feedback effect on central gonadotropin release and subsequent ovarian production of estrogen; however, it is sometimes necessary to use continuous estrogen to control the symptoms. This use of estrogen can often lead to undesirable side effects and even the risk of endometrial cancer.

Another treatment consists of continuous administration of progestins which induces amenorrhea and by suppressing ovarian estrogen production can cause regressions of the endometrial growths. The use of chronic progestin therapy is often accompanied by the unpleasant CNS side effects of progestins and often leads to infertility due to suppression of ovarian function.

A third treatment consists of the administration of weak androgens, which are effective in controlling the endometriosis; however, they induce severe masculinizing effects. Several of these treatments for endometriosis have also been implicated in causing a mild degree of bone loss with continued therapy. Therefore, new methods of treating endometriosis are desirable.

SUMMARY OF THE INVENTION

The invention provides novel benzothiophenes of the formula (I):

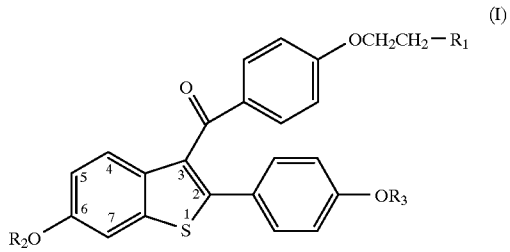

wherein

R$_1$ is N-pyrrolidinyl or N-piperidinyl;

R$_2$ and R$_3$ are independently hydrogen, —CO—(C$_{10}$–C$_{22}$ alkyl), —CO—(C$_{10}$–C$_{22}$ branched alkyl), —CO—(C$_{10}$–C$_{22}$ alkenyl), —CO—(C$_{10}$–C$_{22}$ polyalkenyl), —CO—(C$_{10}$–C$_{22}$ alkynyl), or —CO—(CH$_2$)$_n$COR$_4$; provided R$_2$ and R$_3$ are not both dodecanoyl, and one of R$_2$ or R$_3$ is not hydrogen R$_4$ is -3-cholesteryl or —O(CH$_2$)$_2$(OR$_5$)CH$_2$OR$_6$;

R$_5$ and R$_6$ are independently hydrogen, —CO—(C$_{10}$–C$_{22}$ alkyl), —CO—(C$_{10}$–C$_{22}$ branched alkyl), —CO—(C$_{10}$–C$_{22}$ alkenyl), —CO—(C$_{10}$–C$_{22}$ polyalkenyl), or —CO—(C$_{10}$–C$_{22}$ alkynyl); provided one of R$_5$ or R$_6$ is not hydrogen;

n is 0–4; and pharmaceutically acceptable salts and solvates thereof.

Included within the scope of compounds of formula I are isomers of asymmetric centers and cis/trans isomers associated with alkenyl moieties.

The present invention further relates to pharmaceutical compositions containing compounds of formula I, optionally containing estrogen or progestin, and the use of such compounds, alone, or in combination with estrogen or progestin, for alleviating the symptoms of post-menopausal syndrome, particularly osteoporosis, cardiovascular related pathological conditions, and estrogen-dependent cancer. As used herein, the term "estrogen" includes steroidal compounds having estrogenic activity such as, for example 17β-estradiol, estrone, conjugated estrogen (Premarin®), equine estrogens, 17β-ethynyl estradiol, and the like. As used herein, the term "progestin" includes compounds having progestational activity such as, for example, progesterone, norethylnodrel, nongestrel, megestrol acetate, norethindrone, and the like.

Further, this invention provides for a method of administration of a compound of formula I at the site of an atherosclerotic plaque.

This invention also provides for methods of use of the compounds of formula I for the local treatment and prevention of restenosis administered during the angioplasty of atherosclerotic plaques.

DETAILED DESCRIPTION OF THE INVENTION

The current invention relates to the discovery of a new series of lipophilic esters of 2-phenyl-3-aroylbenzo[b] thiophenes shown in formula I. These compounds are useful for treating or preventing restenosis, particularly by administration at a local site, following angioplasty of an atherosclerotic plaque, as well as inhibiting pathological conditions associated with post-menopausal syndrome.

The term "inhibit" includes its generally accepted meaning which includes prohibiting, preventing, restraining, and slowing, stopping, or reversing progression, severity, or a resultant symptom. As such, the methods include both medical therapeutic and/or prophylactic administration, as appropriate.

The general chemical terms used in the description of a compound of formula I have their usual meanings. For example, the term "—CO(C$_{10–22}$ alkyl or C$_{10}$–C$_{22}$ branched alkyl)" would include —CO(C$_{14}$–C$_{22}$ alkyl) and —CO (C$_{14}$–C$_{22}$ branched alkyl), and groups such as decanoyl, undecanoyl, lauroyl, myristoyl, palmitoyl, stearoyl, arachidoyl, 2,2-dimethylundecanoyl, d,l-2-ethylundecanoyl, and the like. The term "C$_{10}$–C$_{22}$ alkenyl or C$_{10}$–C$_{22}$ polyalkenyl" would include groups such as: palmitoleoyl, oleoyl, linoleoyl, linolenoyl, arachidonoyl, and the like, including natural and un-natural cis/trans isomers. The term "C$_{10}$–C$_{22}$ alkynyl" would include such groups as 2-alkynyl-undecanoyl, 3-alkynyl-stearoyl, and the like.

The compounds of this invention may be prepared by known and/or analogous chemical synthesis methods well known in the art. Briefly, the starting benzothiophene, such as, raloxifene, can be prepared from readily available starting materials by procedures described in the U.S. Pat. Nos., 4,133,814 and 4,418,068, incorporated herein by reference.

The preparation of the acyl esters of the 4' and 6 phenolic hydroxyls of raloxifene can be accomplished with the use of activated carboxylates of the long chain acids, many of which are commercially available. Examples of such activated carboxylic acids are: stearoyl chloride, stearoyl anhydride, plamitoyl chloride, arachidonoyl chloride, and the like. The acylation reaction may be carried out in a variety of aprotic solvents such as THF, DMF, EtOAc, ether, benzene, toluene, or halogenated solvents such as chloroform or methylenechloride. THF is a preferred solvent.

The reaction may be carried in the presence of an acid scavenger such as triethylamine, pyridine, or the like. Triethylamine is a preferred base. Additionally, an acylation catalyst such as 4-dimethylaminopyridine can be used. The acylation reaction may be carried out under a variety of reaction conditions from 0°–100° C. and under a nitrogen atmosphere. Usually, ambient temperature is sufficient. The reaction times can be from 1–36 hours depending on the nature of the acylating moiety and other reaction conditions, progress of the reaction can be monitored by techniques such as tlc. The resulting products are purified by evaporation of the reaction solvent in vacuo and re-dissolving the residue, in EtOAc. The EtOAc solution is washed with aqueous base (1N NaOH) and then with water and dried by filtration through anhydrous Na$_2$SO$_4$ or MgSO$_4$. The resulting organic solution is evaporated to a solid in vacuo. The final product is then obtained by chromatographing the crude mixture on a silica gel column eluted with mixtures of EtOAc-hexane or the like. A preferred solvent combination is 80% EtOAc-hexane. The appropriate fractions containing the desired product may be identified by tlc and these fractions combined and evaporated to dryness in vacuo.

Mono- and di-esters of this invention may be prepared by using either one or two equivalents of the appropriate acylating reagent. The use of one equivalent of acylating reagent gives rise to a statistical distribution of: dihydroxy (raloxifene, starting material), 4'hydroxy-6-acylraloxifene, 4'-acyl-6-hydroxyraloxifene, and 4',6-diacylraloxifene. These compounds are easily separated by chromatographic procedures, silica gel eluted with mixtures of EtOAc and hexane. Thus, the various mono-derivatives may be obtained. The long-chain ester of formula I are tan, oily, and amorphous solids, or thick oils.

Mono- or di-glycerides, and 3-cholesterol derivatives of formula I may be prepared by using a "linker" dicarboxylic acid. This moiety links the phenolic hydroxyls of the starting material (raloxifene) to the alcoholic hydroxyl of the mono- or di-glyceride or cholesterol via carboxylic esters. Examples of such "linking" dicarboxylic acids are oxaloyl, succinoyl, glutaroyl, etc. The formation of such di-esters are well known in the art.

Briefly, activated carboxylic acid moieties such as oxaloyl chloride, succinic anhydride, or glutaric anhydride can be used. Succinic anhydride is preferred.

In a manner similar to the formation of the acid esters described above, the mono- or preferred di-succinates of raloxifene are prepared. The free carboxylic acid moieties can further activated to react with alcoholic hydroxyls of cholesterol or mono- or di-glycerides. The activation of these free carboxylic acids may be accomplished by formation of mixed anhydrides with alkylchloroformates (i-butylchloroformate) and the intermediate mixed anhydride reacted with the appropriate alcohol. Similarly, the free carboxyls may be directly esterified with the appropriate alcohol using a dehydrating agent such as DCC (dicyclohexylcarbodimide) in an appropriate aprotic solvent such as THF. Alternately, the "linking" dicarboxylic esters can be prepared by first, esterifying the lipophyllic alcohol, e.g., cholesterol, and then forming the other ester bond with the phenol of raloxifene. The final purified compounds of formula I can be obtained by chromatographic techniques. These compounds are oils or oily, amorphous solids.

Preferred embodiments of this invention are 4',6-distearoyl raloxifene or ([6-stearoyloxy-2-[4-(stearoyloxy)phenyl]benzo[b]thien-3-yl][4-(2-(1-piperidenyl)ethoxy)phenyl] methanone); 4',6-di-[3-cholesterolatesuccinoyl] raloxifene; and 4',6-di-[1,2-di-stearoyl-3-glycerolsuccinate] raloxifene.

Below are described detailed preparations of selected compounds of formula I. These descriptions are for the purpose of illustration and are not meant to be limiting to the scope of this invention.

EXAMPLE 1

[6-Stearoyloxy-2-[(4-stearoyloxy)phenyl]benzo[b]thien-3-yl][4-(2-(1-piperidenyl)ethoxy)phenyl] methanone (4',6-Distearoyl raloxifene)

A suspension of 2.6 g (0.005 mol) of raloxifene hydrochloride in 250 mL of THF was prepared. To this was added 11 g (0.1 mol) of triethylamine and 20 mg of dimethylaminopyridine (DMAP). The reaction mixture was allowed to stir for 10 minutes at ambient temperature under an atmosphere of nitrogen. Stearoyl chloride, 3.3 g (0.011 mol), was added and the reaction was allowed to proceed for sixteen hours. The reaction mixture was evaporated to dryness in vacuo and resuspended in 100 mL of EtOAc. The EtOAc suspension was washed with water, then 1N NaOH, and finally with water. The organic layer was dried by filtration through anhydrous $Na_2SO_4$ and evaporated to dryness. The crude product was further purified by chromatography on a silica gel column eluted with EtOAc. Evaporation of the desired fractions yielded 1.46 g of the title compound as a oily, low melting solid.

PMR: consistent with the proposed structure

MS: m/e=1006 FD

EA: Calc: C, 76.37; H, 9.51; N, 1.39 Found: C, 76.17; H, 9.56; N, 1.56 $C_{64}H_{95}NO_6S$.

EXAMPLE 2

4',6-Dilinolenoyl Raloxifene

This derivative was prepared in a manner similar to Example 1, using 2.6 g (0.005 mol) of Raloxifene HCl, 2 g (0.02 mol) of triethylamine, 20 mg of DMAP, and 3.2 g (0.01 mol) of linolenoyl chloride in 250 mL of THF. The final product was chromatographed on a silica gel column eluted with EtOAc-hexane (8:2). This yielded 3.21 g of the title compound as clear oil.

PMR: consistent with the proposed structure

MS: m/e=994 FD.

EXAMPLE 3

4',6-Dilinoleoyl Raloxifene

The derivative was prepared in a manner similar to that in example 2, using 2.6 g (0.005 mol) of Raloxifene HCl, 3 g (0.03 mol) of triethylamine, 20 mg of DMAP, and 3.2 g (0.01 mol) of linoleoyl chloride in 250 mL of THF. This yielded 4.76 g of the title compound as thick oil.

PMR: consistent with proposed structure

MS: m/e=998 FD

EXAMPLE 4

4',6-Dimyristoyl Raloxifene

This derivative was prepared in a manner similar to that in example 2, using 2.6 g (0.005 mol) of Raloxifene HCl, 5 g (0.05 mol) of triethylamine, 20 mg of DMAP, and 2.8 g (0.012 mol) of myristoyl chloride in 250 mL of THF. This yielded 2.61 g of the title compound as thick oil which solidified upon standing at room temperature.

PMR: consistent with proposed structure

MS: m/e=893 FD

EXAMPLE 5

4',6-Dipalmitoyl Raloxifene

This derivative was prepared in a manner similar to that in example 2, using 2.6 g (0.005 mol) of Raloxifene HCl, 5 g (0.05 mol) of triethylamine, 20 mg of DMAP, and 3.3 g (0.012 mol) of palmitoyl chloride in 250 mL of THF. This yielded 1.25 g of the title compound as a thick oil which solidified upon standing at room temperature.

PMR: consistent with proposed structure

MS: m/e=949 FD

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, pharmaceutically acceptable salts thus include acetate, phenylacetate, trifluoracetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methane-sulfonate, naphthalene-1-sulfonate, naphthalene-2-sulfonate, p-toluenesulfonate, xylenesulfonate, tartarate, and the like. A preferable salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates and bicarbonates, as well as aliphatic and aromatic amines, aliphatic diamines and hydroxy alkylamines. Bases especially useful in the preparation of additional salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parental administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes. alleviating post-menopausal syndrome in women which comprises the aforementioned method using compounds of Formula I and further comprises administering to a woman an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, infra, indicates that the combination treatments are useful for alleviating the symptoms of post-menopausal symptoms in women.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin, and norethylnodrel and norethindrone are preferred progestin-based agents.

The method of administration of each estrogen- and progestin-based agent is consistent with that which is known in the art. For the majority of the methods of the present invention, compounds of Formula I are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 80 mg/day.

The local delivery of inhibitory amounts of active compound for the treatment of restinosis can be by a variety of techniques which administer the compound at or near the proliferative site. Examples of local delivery techniques are not intended to be limiting but to be illustrative of the techniques available. Examples include local delivery catheters, site specific carriers, implants, direct injection, or direct applications.

Local delivery by a catheter, including a permeable membrane catheter, allows the administration of a pharmaceutical agent directly to the proliferative lesion. Examples of local delivery using a balloon catheter are described in EPO 383 492 A2 and U.S. Pat. No. 4,636,195 (Wolinsky, Jan. 13, 1987).

Local delivery by an implant describes the surgical placement of a matrix that contains the pharmaceutical agent into the proliferative lesion. The implanted matrix releases the pharmaceutical agent by diffusion, chemical reaction, or solvent activators. Lange, *Science* 249: 1527–1533 (September, 1990).

An example of local delivery by an implant is the use of a stent. Stents are designed to mechanically prevent the collapse and reocclusion of the coronary arteries. Incorporating a pharmaceutical agent into the stent delivers the drug directly to the proliferative site. Local delivery by this technique is described in Kohn, *Pharmaceutical Technology* (October, 1990).

Another example is a delivery system in which a polymer that contains the pharmaceutical agent is injected into the lesion in liquid form. The polymer then cures to form the implant in situ. This technique is described in PCT WO 90/03768 (Donn, Apr. 19, 1990).

Another example is the delivery of a pharmaceutical agent by polymeric endoluminal sealing. This technique uses a catheter to apply a polymeric implant to the interior surface of the lumen. The pharmaceutical agent incorporated into the biodegradable polymer implant is thereby released at the surgical site. It is described in PCT WO 90/01969 (Schindler, Aug. 23, 1989).

A final example of local delivery by an implant is by direct injection of vesicles or microparticulates into the proliferative site. These microparticulates may be composed of substances such as proteins, lipids, carbohydrates or synthetic polymers. These microparticulates have the pharmaceutical agent incorporated throughout the microparticle or over the microparticle as a coating. Delivery systems incorporating microparticulates are described in Lang, Science 249: 1527–1533 (September, 1990) and Mathiowitz, et al., *J. App. Poly. Sci.,* 26:809 (1981).

Local delivery by site specific carriers describes attaching the pharmaceutical agent to a carrier which will direct the drug to the proliferative lesion. Examples of this delivery technique includes the use of carriers such as a protein ligand or a monoclonal antibody. Lange, *Science* 249: 1527–1533 (September).

Local delivery by direct application includes the use of topical applications. An example of a local delivery by direct application is applying the pharmaceutical agent directly to the arterial bypass graft during the surgical procedure.

Another aspect of this invention are efficacious formulations of the compounds of formula I for delivery into the highly lipophilic environment of the atherosclerotic plaque. Usual formulations of the type used for intravenous injections (normally aqueous solutions) are inadvisable in light of the environment of the target site (plaque). The major considerations involving the formulation are 1) the formulated product must pumped through the angioplasty catheter, 2) the formulated product must facilitate the penetration of a compound of formula I into the lipophyllic matrix of the plaque, and 3) the formulated product must have minimal toxicity.

Carrier agents which would produce flowable solutions of a compound of formula I are DMSO, glycerol, liquid poly-alcohols, low molecular weight oils, and the like. These liquids may be adjusted with small amounts of water or alcohols to lower their viscosity. Additional agents such as cyclodextrins may be useful to aid the dissolution of the compounds of formula I in the carrier.

Penetration agents would facilitate entry into the plaque and include detergents such as tritons, organophosphates, organosulfates, carboxymethylcellulose, DMSO, and the like.

Also, trace quantities of radio-contrasting agent or dye may be incorporated into the formulations to aid the attending physician to verify the effective delivery of the formulation to its intended target site.

The exact amount of a compound of formula I and the volume of the formulated product for use in inhibiting atherosclerotic plaque at the local site may vary depending the circumstances and is best determined by the attending physician. Such factors as the depth and size of the atherosclerotic plaque to be treated are highly variable, in general, 0.5–2.0 mg would be an effective amount of a compound of formula I and this to be delivered in a volume of 1–3 mL. Thus various strengths and volumes of these formulations would be necessary to allow the greatest latitude of choice to the attending physician.

The clinical use of this invention would not differ greatly from the standard angioplastic procedure currently in practice. An additional benefit of this invention, due to the inclusion of a radio-contrasting agent in the formulated product, is that the attending physician may verify the location and the extent of penetration of the formulation into the plaque and surrounding tissue by radiographic techniques.

Listed below are formulations for the compounds of formula I. These formulations are given for purposes of illustration and are not intended to limit the scope of this invention in anyway. The term "active ingredient" means a compound of formula I.

Formulation 1

| Ingredient | Quantity (mg/capsule) |
| --- | --- |
| Active Ingredient | 0.5–3.0 mg |
| B-cyclodextrin | 0.1 mg |
| DMSO | 1.5 mL |
| Barium Oxide | 0.1 mg |
| Sterile Water | |

A compound of formula I (0.5–3.0 mg) and 0.1 mg of B-cyclodextrin is dissolved in 1.5 mL of DMSO and 0.1 mg of barium oxide is added. The mixture is heated to induce solution (50° C.) and allowed to cool to ambient temperature. Sterile water is added to bring the volume to 2 mL.

Formulation 2

| Ingredient | Quantity (mg/capsule) |
| --- | --- |
| Active Ingredient | 0.5–3.0 mg |
| glycerol | 1 mL |
| DMSO | 1 mL |
| Triton X | 0.1 mg |
| Barium Oxide | 0.1 mg |

A compound of formula I (0.5–3.0 mg) is dissolved in 1 mL of DMSO. Triton X (0.1 mg) and barium oxide (0.1 mg)

are added along with 1 mL of glycerol. The mixture is thoroughly mixed.

Formulation 3: Gelatin Capsules
Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 4: Tablets

| Ingredient | Quantity (mg/tablet) |
|---|---|
| Active Ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 5: Tablets

| Ingredient | Quantity (mg/tablet) |
|---|---|
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 6: Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 7: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 8: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 9: Intravenous Solution

| Ingredient | Quantity |
|---|---|
| Active ingredient | 50 mg |
| Isotonic saline | 1,000 mL |

The solution of the above ingredients is intravenously administered to a patient at a rate of about 1 mL per minute.

Formulation 10: Combination Capsule I

| Ingredient | Quantity (mg/capsule) |
|---|---|
| Active ingredient | 50 |
| Premarin | 1 |
| Avicel pH 101 | 50 |
| Starch 1500 | 117.50 |
| Silicon Oil | 2 |

-continued

| Ingredient | Quantity |
|---|---|
| Tween 80 | 0.050 |
| Cab-O-Sil | 0.25 |

Formulation 11: Combination Capsule II

| Ingredient | Quantity (mg/capsule) |
|---|---|
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

Formulation 12: Combination Tablet

| Ingredient | Quantity (mg/capsule) |
|---|---|
| Active ingredient | 50 |
| Premarin | 1 |
| Corn Starch NF | 50 |
| Povidone, K29–32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

More generally, the total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

As mentioned previously, one of the novel aspects of this invention is the enhanced lipophillicity of compounds of formula I. Experimental demonstration of this enhanced lipophillicity, and thus enhanced ability to penetrate an atherosclerotic plaque, may be shown by several techniques: 1) excellent solubility of the compounds of formula I in lipophillic solvents such as EtOAc, 2) excellent lipophillic character of the compounds of formula I as shown by a standard, chemical technique such as $\log_p$ partion coefficients (n-octanol/water), or 3) enhanced diffusion rates of the compounds of formula I into a lipophillic matrix such as cholesterol.

The following assays are used to illustrate the invention:

Balloon Injury of Carotid Arteries

Balloon injury to the left common carotid arteries of male, Sprague-Dawley rats (350–400 g) is accomplished by three passes of an inflated 2F Fogarty balloon catheter (Baxter Healthcare, McGraw Park, Ill.) as described by Clowes A. W., et al., Lab. Invest. 49, p.208–215 (1983). Animals are anesthetized with Ketamine (80 mg/kg, IM) and Rompun (16 mg/kg, IM). Entry of the balloon catheter to the left common carotid artery is made by a nick in the external carotid artery, which is tied off at the end of the surgical procedure.

Following balloon injury, a single daily dose of a compound of formula I is applied to the exterior of the injured carotid artery as a "loading dose" of drug in a small volume (120 uL). Subsequent to this, continuous delivery of the compound to the adventitial (exterior) space surrounding the injured carotid artery is accomplished by means of a miniosmotic pump (Alzet, 2ML2, Palo Alto, Calif.) implanted subcutaneously in the back of the rat. Pumps are primed before surgery and implanted immediately following balloon injury. Dosing solutions are delivered to the adventitial space via a micro-renathane catheter (MRE-40). The catheter is sutured in place with two ligatures (4-0 silk) to the left external carotid artery, and the tip is positioned to deliver the drug solutions at the midpoint of the common carotid artery. The dosing vehicle employed in this study is 20% cyclodextrin in sterile water.

Fourteen days post surgery, animals are anesthetized (vide supra) and perfused through the abdominal aorta in a retrograde manner at physiological pressure with a zinc formalin fixative (Anatech LTD, Battle Creek, Mich.). Middle sections (5 mm) of the carotids are removed from the animals, processed, and embedded in paraffin. Three adjacent cross sections (5 um thick) of each vessel are cut, stained with hematoxylin and eosin, and cross sectional intimal areas are quantitated with an image analyzer (Quantimat 970, Cambridge Inst. Cambridge. UK).

The results of this experiment demonstrate the ability of the compounds of formula I to inhibit the reduction of intimal area due to restenosis initiated by injury of the balloon catheter.

In the examples illustrating the methods, a postmenopausal model is used in which effects of different treatments upon circulating lipids are determined.

Seventy-five day old female Sprague Dawley rats (weight range of 200 to 225 g) are obtained from Charles River Laboratories (Portaae, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and had ad libitum access to food (calcium content approximately 0.5%) and water for one week. Room temperature is maintained at 22.2°±1.7° C. with a minimum relative humidity of 40%. The photoperiod in the room is 12 hours light and 12 hours dark.

Dosing Regimen Tissue Collection.

After a one week acclimation period (therefore, two weeks post-OVX) daily dosing with test compound is initiated. 17α-ethynyl estradiol or the test compound are given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine:Xylazine (2:1, V:V) mixture and a blood sample is collected by cardiac puncture. The animals are then sacrificed by asphyxiation with $CO_2$, the uterus is removed through a midline incision, and a wet uterine weight is determined.

Cholesterol Analysis.

Blood samples are allowed to clot at room temperature for 2 hours, and serum is obtained following centrifugation for 10 minutes at 3000 rpm. Serum cholesterol is determined using a Boehringer Mannheim Diagnostics high performance cholesterol assay. Briefly the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Uterine Eosinophil Peroxidase (EPO) Assay.

Uteri are kept at 4° C. until time of enzymatic analysis. The uteri are then homogenized in 50 volumes of 50 mM Tris buffer (pH—8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosonophils in the uterus is an indication of estrogenic activity of a compound. The maximal velocity of a 15 second interval is determined over the initial, linear portion of the reaction curve.

Source of Compound:

17α-ethynyl estradiol is obtained from Sigma Chemical Co., St. Louis, Mo.

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the present invention and ethynyl estradiol ($EE_2$) in 20% hydroxypropyl β-cyclodextrin are orally administered to test animals.

MCF-7 Proliferation Assay

MCF-7 breast adenocarcinoma cells (ATCC HTB 22) are maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 ug/mL) (maintenance medium). Ten days prior to assay, MCF-7 cells are switched to maintenance medium supplemented with 10% dextran coated charcoal stripped fetal bovine serum (DCC-FBS) assay medium) in place of 10% FBS to deplete internal stores of steroids. MCF-7 cells are removed from maintenance flasks using cell dissociation medium (Ca++/Mg++ free HBSS (phenol red-free) supplemented with 10 mM HEPES and 2 mM EDTA). Cells are washed twice with assay medium and adjusted to 80,000 cells/mL. Approximately 100 μL (8,000 cells) are added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control are prepared in assay medium and 50 μL transferred to triplicate microcultures followed by 50 μL assay medium for a final volume of 200 μL. After an additional 48 hours at 37° C. in a 5% $CO_2$ humidified incubator, microcultures are pulsed with tritiated thymidine (1 uCi/well) for 4 hours. Cultures are terminated by freezing at −70° C. for 24 hours followed by thawing and harvesting of microcultures using a Skatron Semiautomatic Cell Harvester. Samples are counted by liquid scintillation using a Wallac BetaPlace β counter.

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

Uterine Fibrosis Test Procedures

Assay 1

Between 3 and 20 women having uterine fibrosis are administered a compound of the present invention. The amount of compound administered is from 0.1 to 1000 mg/day, and the period of administration is 3 months.

The women are observed during the period of administration, and up to 3 months after discontinuance of administration, for effects on uterine fibrosis.

Assay 2

The same procedure is used as in Test 1, except the period of administration is 6 months.

Assay 3

The same procedure is used as in Test 1, except the period of administration is 1 year.

Assay 4

A. Induction of fibroid tumors in guinea pig.

Prolonged estrogen stimulation is used to induce leiomyomata in sexually mature female guinea pigs. Animals are dosed with estradiol 3–5 times per week by injection for 2–4 months or until tumors arise. Treatments consisting of a compound of the invention or vehicle is administered daily for 3–16 weeks and then animals are sacrificed and the uteri harvested and analyzed for tumor regression.

B. Implantation of human uterine fibroid tissue in nude mice.

Tissue from human leiomyomas are implanted into the peritoneal cavity and or uterine myometrium of sexually mature, castrated, female, nude mice. Exogenous estrogen are supplied to induce growth of the explanted tissue. In some cases, the harvested tumor cells are cultured in vitro prior to implantation. Treatment consisting of a compound of the present invention or vehicle is supplied by gastric lavage on a daily basis for 3–16 weeks and implants are removed and measured for growth or regression. At the time of sacrifice, the uteri is harvested to assess the status of the organ.

Assay 5

A. Tissue from human uterine fibroid tumors is harvested and maintained, in vitro, as primary nontransformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the present invention and vehicle. Levels of steroid hormone receptors are assessed weekly to determine whether important cell characteristics are maintained in vitro. Tissue from 5–25 patients are utilized.

Activity in at least one of the above tests indicates the compounds of the present invention are of potential in the treatment of uterine fibrosis.

Endometriosis Test Procedure

In Tests 1 and 2, effects of 14-day and 21-day administration of compounds of the present invention on the growth of explanted endometrial tissue can be examined.

Assay 1

Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed.

On the day following surgery, animals in Groups 1 and 2 receive intraperitoneal injections of water for 14 days whereas animals in Group 3 receive intraperitoneal injections of 1.0 mg of a compound of the present invention per kilogram of body weight for the same duration. Following 14 days of treatment, each female is sacrificed and the endometrial explants, adrenals, remaining uterus, and ovaries, where applicable, are removed and prepared for histological examination. The ovaries and adrenals are weighed.

Assay 2

Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow.

Approximately 50 days following surgery, animals assigned to Group 1 receive intraperitoneal injections of water for 21 days whereas animals in Group 2 receive intraperitoneal injections of 1.0 mg of a compound of the present invention per kilogram of body weight for the same duration. Following 21 days of treatment, each female is sacrificed and the endometrial explants and adrenals are removed and weighed. The explants are measured as an indication of growth. Estrous cycles are monitored.

Assay 3
A. Surgical induction of endometriosis

Autographs of endometrial tissue are used to induce endometriosis in rats and/or rabbits. Female animals at reproductive maturity undergo bilateral oophorectomy, and estrogen is supplied exogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric lavage on a daily basis for 3–16 weeks, and implants are removed and measured for growth or regression. At the time of sacrifice, the intact horn of the uterus is harvested to assess status of endometrium.

B. Implantation of human endometrial tissue in nude mice.

Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of a compound of the present invention supplied by gastric lavage on a daily basis for 3–16 weeks, and implants are removed and measured for growth or regression. At the time of sacrifice, the uteri is harvested to assess the status of the intact endometrium.

Assay 4

A. Tissue from human endometrial lesions is harvested and maintained in vitro as primary nontransformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the invention, and vehicle. Levels of steroid hormone receptors are assessed weekly to determine whether important cell characteristics are maintained in vitro. Tissue from 5–25 patients is utilized.

Activity in any of the above assays indicates that the compounds of the present invention are useful in the treatment of endometriosis.

Inhibition of Aortal Smooth Cell Proliferation/
Restenosis Test Procedure

Compounds of the present invention have capacity to inhibit aortal smooth cell proliferation. This can be demonstrated by using cultured smooth cells derived from rabbit aorta, proliferation being determined by the measurement of DNA synthesis. Cells are obtained by explant method as described in Ross, *J. of Cell Bio.* 50: 172 (1971). Cells are plated in 96 well microtiter plates for five days. The cultures become confluent and growth arrested. The cells are then transferred to Dulbecco's Modified Eagle's Medium (DMEM) containing 0.5–2% platelet poor plasma, 2 mM L-glutamine, 100 U/ml penicillin, 100 mg ml streptomycin, 1 mC/ml $^3$H-thymidine, 20 ng/ml platelet-derived growth factor, and varying concentrations of the present compounds. Stock solution of the compounds is prepared in dimethyl sulphoxide and then diluted to appropriate concentration (0.01–30 mM) in the above assay medium. Cells are then incubated at 37° C. for 24 hours under 5% $CO_2$/95% air. At the end of 24 hours, the cells are fixed in methanol. $^3$H thymidine incorporation in DNA is then determined by scintillation counting as described in Bonin, et al., *Exp. Cell Res.* 181: 475–482 (1989).

Inhibition of aortal smooth muscle cell proliferation by the compounds of the present invention are further demonstrated by determining their effects on exponentially growing cells. Smooth muscle cells from rabbit aortae are seeded in 12 well tissue culture plates in DMEM containing 10% fetal bovine serum, 2 mM L-glutamine, 100 U/ml penicillin, and 100 mg/ml streptomycin. After 24 hours, the cells are attached and the medium is replaced with DMEM containing 10% serum, 2 mM L-glutamine, 100 U/ml penicillin, 100 mg/ml streptomycin, and desired concentrations of the compounds. Cells are allowed to grow for four days. Cells are treated with trypsin and the number of cells in each culture is determined by counting using a ZM-Coulter counter.

Activity in the above assays indicates that the compounds of the present invention are of potential in the treatment of restenosis.

We claim:

1. A method of inhibiting pathological conditions resulting from an estrogen deficiency which comprises administering to a human in need thereof a compound of the formula (I):

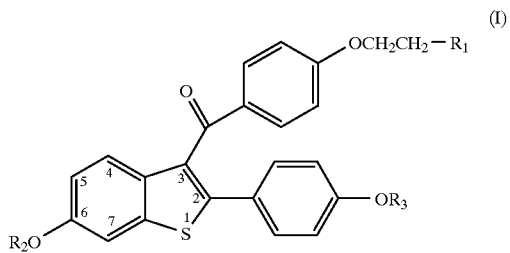

wherein $R_1$ is N-pyrrolidinyl or N-piperidinyl;

$R_2$ and $R_3$ are independently hydrogen, —CO—($C_{10}$–$C_{22}$ alkyl), —CO—($C_{10}$–$C_{22}$ branched alkyl), —CO—($C_{10}$–$C_{22}$ alkenyl), —CO—($C_{10}$–$C_{22}$ polyalkenyl), —CO—($C_{10}$–$C_{22}$ alkynyl), or —CO—$(CH_2)_n COR_4$;

provided that when $R_1$ is N-piperidinyl, neither $R_2$ or $R_3$ is —CO—($C_{10}$–$C_{15}$ alkyl) or —CO—($C_{10}$–$C_{15}$ branched alkyl); and provided one of $R_2$ or $R_3$ is not hydrogen;

$R_4$ is -3-cholesteryl or —O$(CH_2)_2(OR_5)CH_2OR_6$;

$R_5$ and $R_6$ are independently hydrogen, —CO—($C_{10}$–$C_{22}$ alkyl), —CO—($C_{10}$–$C_{22}$ branched alkyl), —CO—($C_{10}$–$C_{22}$ alkenyl), —CO—($C_{10}$–$C_{22}$ polyalkenyl), or —CO—($C_{10}$–$C_{22}$ alkynyl); provided one of $R_5$ or $R_6$ is not hydrogen;

n is 0–4; or a pharmaceutically acceptable salt or solvate thereof.

2. A method of claim 1 wherein $R_1$ is n-piperidinyl and $R_2$ and $R_3$ are each stearoyl.

3. A method of claim 1 wherein $R_1$ is n-piperidinyl and $R_2$ and $R_3$ are 3-cholesterylsuccinoyl.

4. A method of claim 1 wherein $R_1$ is n-piperidinyl and $R_2$ and $R_3$ are 1,2-di-stearoylglycerol-3-succinoyl.

5. A method of claim 1 where said compound is selected from the group consisting of 4',6-distearoylraloxifene, 4',6-di-[3-cholesterolate succinoyl]raloxifene, or 4',6-di-[1,2-di-stearoyl-3-glycerol succinate]raloxifene.

6. A method according to claim 1 wherein the pathological condition resulting from an estrogen deficiency is osteoporosis.

7. A method according to claim 1 wherein the pathological condition resulting from an estrogen deficiency is related to a cardiovascular disease.

8. A method according to claim 7 wherein the cardiovascular disease is hyperlipidemia.

* * * * *